United States Patent [19]

Sato et al.

[11] Patent Number: 5,491,254
[45] Date of Patent: Feb. 13, 1996

[54] PROSTAGLANDIN DERIVATIVES

[75] Inventors: Fumie Sato, 1-219, Kugenumahigashi 3-Chome, Fujisawa-shi, Kanagawa 251; Takehiro Amano, Tokyo; Kazuya Kameo, Tokyo; Tohru Tanami, Tokyo; Masaru Mutoh, Tokyo; Naoya Ono, Tokyo; Jun Goto, Tokyo, all of Japan

[73] Assignees: Taisho Pharmaceutical Co., Ltd.; Fumie Sato, both of Japan

[21] Appl. No.: 373,226

[22] Filed: Jan. 19, 1995

[30] Foreign Application Priority Data

Jul. 24, 1992 [JP] Japan ................................. 4-198556

[51] Int. Cl.⁶ ..................... C07C 177/00; A61K 31/557
[52] U.S. Cl. ............................... 560/121; 562/503
[58] Field of Search ........................... 560/121; 562/503; 514/530, 573

[56] References Cited

U.S. PATENT DOCUMENTS 5,204,371  4/1993  Skuballa et al. ................... 560/121

FOREIGN PATENT DOCUMENTS 115844  2/1983  European Pat. Off. .

2950027  12/1979  Germany .
2502009  5/1990  Japan .
92/18473  10/1992  WIPO .
94/02457  2/1994  WIPO .
94/05631  3/1994  WIPO .
9408959  4/1994  WIPO .
94/19319  9/1994  WIPO .

*Primary Examiner*—Paul J. Killos
*Attorney, Agent, or Firm*—Lorusso & Loud

[57] ABSTRACT

Object

Novel PG derivatives having an excellent platelet aggregation inhibition activity are provided.
Construction Prostaglandin derivatives represented by formula:

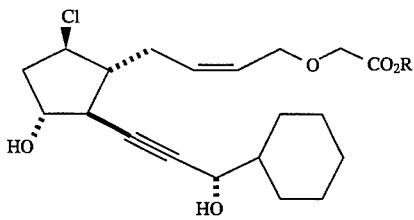

and salts thereof.

3 Claims, No Drawings

PROSTAGLANDIN DERIVATIVES

This application is a 371 of PCT/JP93/00938 Jul. 8, 1993.

TECHNICAL FIELD

The present invention relates to novel prostaglandin (hereinafter abbreviated as PG) derivatives.

BACKGROUND ART

PG exhibits a variety of important physiological activities in a trace amount. For its diversity, natural PG analogues and a vast number of derivatives thereof have been studied on synthesis and biological activities, with attempts to apply these compounds to pharmaceuticals. These studies are reported in many publications and Japanese Patent Application KOKAI No. 52-100446, Japanese Patent Application KOHYO No. 2-502009 (WO 89/00559), etc.

The compounds of the present invention are broadly covered by Formula I described in Japanese Patent Application KOHYO No. 2-502009 supra but there is no specific description on these compounds in the specification.

An object of the present invention is to provide compounds which possess much more potent pharmacological activities than PG derivatives known so far.

Disclosure of Invention

As a result of extensive studies, the present inventors have found that some particular compounds exhibit extremely excellent activities for improving renal diseases, ischemic heart diseases and heart failure, though these compounds broadly fall within Formula I but are not concretely described in the specification supra. The present invention has thus been attained.

That is, the present invention relates to PG derivatives represented by formula:

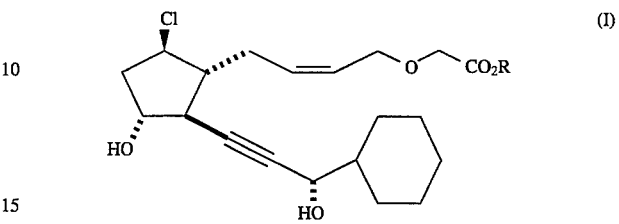

wherein R represents a hydrogen atom or an alkyl group having 1 to 6 carbon atoms, and salts thereof.

In the present invention, the alkyl group is used to mean a straight or branched alkyl group.

The compounds of the present invention shown by formula (I) can be prepared by, e.g., the following processes.

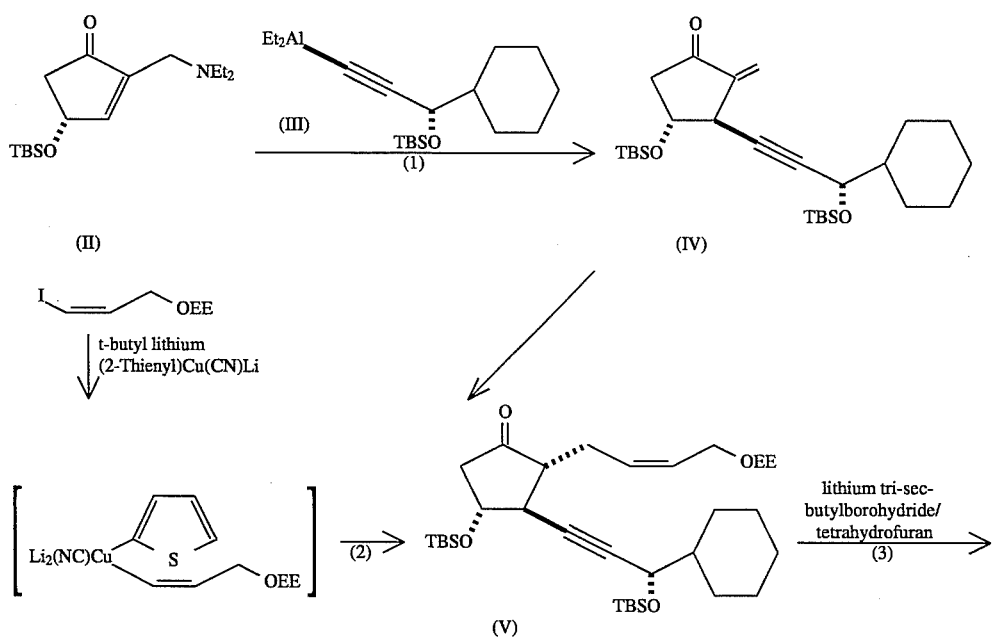

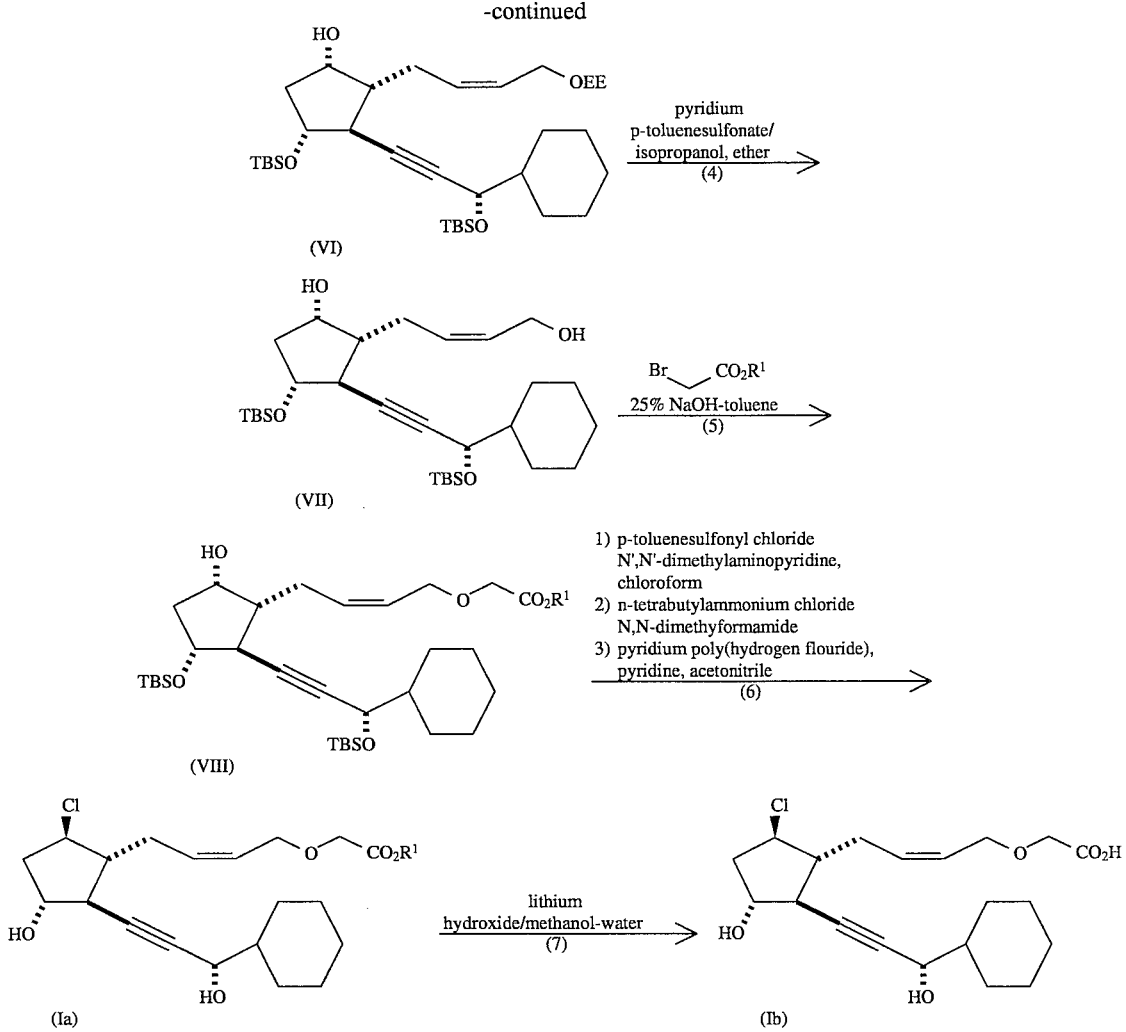

wherein $R^1$ has the same significance as R, except for a hydrogen atom; TBS represents a t-butyldimethylsiloxy group; and EE represents an ethoxyethyl group.

That is, the compound of formula (II) is reacted with the compound of formula (III) to introduce the w-side chain of PG and thus obtain the compound of formula (IV). On the other hand, (Z)-1-iodo-3-(1-ethoxyethyloxy)-1-propene is reacted with t-butyl lithium and lithium 2-thienylcyanocuprate. The resulting product is reacted with the compound of formula (IV) obtained above, Whereby the s-side chain of PG is introduced to give the compound of formula (V). The compound of formula (V) is then reduced stereo-selectively with lithium tri-sec-butylborohydride to obtain the compound of formula (VI). Thereafter the ethoxyethyl protective group is removed to give the compound of formula (VII). The compound of formula (VII) is reacted with a compound represented by formula:

$$Br(CH_2)CO_2R^1$$

wherein $R^1$ has the same significance as defined above, to obtain the compounds of formula (VIII). Then the hydroxy group in the compounds of formula (VIII) is tosylated with p-toluenesulfonyl chloride followed by reacting the tosylated compound with tetra-n-butylammonium chloride. From the resulting chlorosubstituted compound the protective groups of the hydroxy groups are removed with hydrogen fluoride/ pyridine to give the compounds of formula (Ia) (the compounds of formula (I) wherein R is other than a hydrogen atom). The compounds of formula (I) wherein R is a hydrogen atom can be obtained by hydrolyzing the compounds of formula (Ia) (which correspond to the compounds of formula (Ib)) with lithium hydroxide.

BEST MODE FOR CARRYING OUT THE INVENTION

Hereinafter the present invention is described in more detail, with reference to the examples and test examples.

EXAMPLE 1

Preparation of
3-oxa-9-deoxy-9β-chloro-16,17,18,19,20-pentanor-15-cyclohexyl-13,14-didehydro-PGF$_2$α t-butyl ester
(Compound 1)

Note) In the nomenclature of compounds, the term "nor." in "16,17,18,19,20-pentanor" is used to mean that carbon chains at the position are missing (carbon chains from the 16 to 20 position are absent).

(1) In 28.8 ml of benzene was dissolved 3.61 g of (3S)-3-(t-butyldimethylsiloxy)-3-cyclohexylprop-   1-yne. n-Butyl lithium (1.95M, hexane solution, 6.4 ml) was added to the solution at 0° C. The mixture was stirred at the same temperature for 30 minutes. After diethyl aluminum chloride (0.97M, hexane solution, 14.8 ml) was added to the thus obtained solution at 0° C., the temperature was elevated to room temperature. Stirring was continued for 30 minutes at the same temperature.

To the solution was added (4R)-2-(N,N-diethylamino)methyl- 4-(t-butyldimethylsiloxy)cyclopent- 2-en-1-one (0.25M, benzene solution, 38.4 ml) at room temperature. The mixture was stirred for 15 minutes.

While stirring, the reaction solution was poured onto a mixture of 100 ml of hexane, 100 ml of saturated ammonium chloride aqueous solution and 30 ml of 3M hydrochloric acid aqueous solution. Thereafter the organic layer was fractionated and washed with 50 ml of saturated sodium bicarbonate aqueous solution. The organic layer was dried and concentrated. The resulting residue was purified by silica gel column chromatography (developing solvent: hexane: ether= 10:1) to give 3.69 g of (3R,4R)-2-methylene-3-[(3'S)- 3'-(t-butyldimethylsiloxy)-3'-cyclohexylprop-1'-ynyl]- 4-(t-butyldimethylsiloxy)cyclopentan-1-one.

$^1$H-NMR (CDCl$_3$, 200MHz) δ ppm: 0.07, 0.08 and 0.12 (3s, 12H), 0.88 (s, 18H), 0.92–1.92 (m, 11H), 2.32 (dd, J=7.4 Hz, 17.8 Hz, 1H), 2.71 (dd, J=6.5 Hz, 17.8 Hz, 1H), 3.48–3.58 (m, 1H), 4.11 (dd, J=1.4 Hz, 6.2 Hz, 1H), 4.20–4.32 (m, 1H), 5.55 (d, J=2.6 Hz, 1H), 6.13 (d, J=3.0 Hz, 1H).

IR (neat): 2930, 2850, 1735, 1640, 1470, 1380, 1255, 1105, 830, 770 cm$^{-1}$.

(2) A solution of t-butyl lithium in pentane (7.55 ml, 1.7M, 12.84 mmols) was dropwise added at −78° C. to a solution of 1.72 g (6.42 mmols) of (Z)-1-iodo- 3-(1-ethoxyethyloxy)-1-propene in 12.8 ml of ether. After stirring the mixture for 40 minutes, a solution of lithium 2-thienylcyanocuprate in tetrahydrofuran (33.4 ml, 0.25M, 8.35 mmols) was added to the mixture. After stirring at −78° C. for 10 minutes, 20 ml of ethereal solution of 2.04 g (4.28 mmols) of the compound obtained in (1) was dropwise added to the mixture. While stirring, the temperature was elevated to room temperature over a period of about an hour. The reaction solution was poured onto a mixture of 100 ml of hexane and 100 ml of saturated ammonium chloride aqueous solution with stirring. The organic layer was removed and the aqueous layer was extracted with 50 ml of hexane. The resulting organic layer was dried over anhydrous magnesium sulfate and then filtered. The filtrate was concentrated in vacuo. The resulting crude product was purified by silica gel column chromatography (developing solvent: hexane: ether= 6:1) to give 2.17 g of 2-decarboxy- 2,3,16,17,18,19, 20-heptanor-4- (1-ethoxyethyloxy)-15-cyclohexyl- 13,14-didehydro-PGE$_2$ 11,15-bis(t-butyldimethylsilyl ether). 1H-NMR (CDCl$_3$, 300 MHz) δ ppm: 0.07, 0.09, 0.10 and 0.12 (4s, 12H), 0.89 (s, 18H), 1.20 (t, J=7.0 Hz, 3H), 1.31 (d, J=4.7 Hz, 3H), 0.93–1.91 (m, 11H), 2.14 (dd, J=7.3 Hz, 18.3 Hz, 1H), 2.20–2.36 (m, 1H), 2.40–2.58 (m, 2H), 2.60–2.77 (m, 2H), 3.42–3.70 (m, 2H), 4.02–4.21 (m, 3H), 4.23–4.32 (m, 1H), 4.71 (q, J=4.7 Hz, 1H), 5.48–5.72 (m, 2H)

(3) A solution of 1.42 g (2.29 mmols) of the compound obtained in (2) in 20 ml of tetrahydrofuran was cooled to −78° C. and lithium tri-sec-butylborohydride (2.97 ml, 1M tetrahydrofuran solution, 2.97 mmols) was dropwise added to the solution. After stirring at −78° C. for an hour, the temperature was elevated to room temperature over a period of about an hour. After 3 ml of 35% hydrogen peroxide aqueous solution was dropwise added to the reaction mixture, the mixture was stirred at room temperature for 15 minutes. After adding thereto 50 ml of saturated ammonium chloride aqueous solution and 50 ml of ether, the organic layer was removed and the aqueous layer was extracted with 30 ml of ether. The resulting organic layer was dried over anhydrous magnesium sulfate and then filtered. The filtrate was concentrated in vacuo. The resulting crude product was purified by silica gel column chromatography (developing solvent: hexane: ether=2: 1) to give 870 mg of 2-decarboxy 2,3,16,17,18,19,20-heptanor-4- (1-ethoxyethyloxy)-15-cyclohexyl- 13,14-didehydro-PGF$_2$ 11,15-bis(-tbutyldimethylsilyl ether).

$^1$H-NMR (CDCl$_3$, 300MHz) δ ppm: 0.08 and 0.10 (2s, 12H), 0.88 and 0.89 (2s, 18H), 1.00–1.50 (m, 6H), 1.21 (t, J=7.1 Hz, 3H), 1.32 (d, J=5.3 Hz, 3H), 1.50–1.92 (m, 7H), 2.00–2.60 (m, 4H), 3.01 (t, J=7.8 Hz, 1H), 3.40–3.73 (m, 2H), 3.92–4.30 (m, 5H), 4.65–4.82 (m, 1H), 5.50–5.73 (m, 2H), (4) To a solution of 727 mg (1.19 mmol) of the compound obtained in (3) in 6 ml of isopropyl alcohol and 6 ml of ether was added 15 mg (0.06 mmol) of pyridium p-toluenesulfonate. The mixture was stirred for 10 hours at room temperature. After 20 ml of ether and then 30 ml of saturated sodium hydrogencarbonate aqueous solution were added to the reaction mixture, the organic layer was removed and the aqueous layer was extracted twice with 10 ml each of ether. The resulting organic layer was dried over anhydrous magnesium sulfate and then filtered. The filtrate was concentrated in vacuo. The resulting crude product was purified by silica gel column chromatography (developing solvent: hexane: ether=1 :1) to give 550 mg of 2_decarboxy-2,3,16,17, 18,19,20-heptanor- 4-hydroxy-15-cyclohexyl-13,14-didehydro-PGF$_2$α 11,15-bis(t-butyldimethylsilyl ether).

$^1$H-NMR (CDCl$_3$, 300MHz) δ ppm: 0.08, 0.09, 0.10 and 0.11 (4s, 12H) , 0.89 and 0.90 (2s, 18H), 0.93–1.32 (m, 6H), 1.38–1.52 (m, 1H), 1.61–1.93 (m, 6H), 1.95–2.07 (m, 1H), 2.20–2.30 (m, 1H), 2.41–2.75 (m, 4H), 3.88 (dd, J=6.2 Hz, 12.0 Hz, 1H), 4.04–4.13 (m, 2H) , 4.26–4.33 (m, 1H) , 4.38 (dd, J=8.8 Hz, 12.0 Hz, 1H), 5.59 (dr, J=5.0 Hz, 10.8 Hz, 1H), 5.77–5.88 (m, 1H)

$^{13}$C-NMR (CDCl$_3$, 75MHz) δ ppm: 132.2, 129.3, 85.5, 83.7, 80.5, 83.7, 73.9, 67.9, 57.4, 53.1, 45.0, 44.9, 42.8, 28.7, 27.0, 26.5, 26.0, 25.8, 18.3, 17.9, −4.43, −4.77, −4.99.

$[α]_D^{36.0}$−5.00° (c=1. 786, chloroform)

(5) To a solution of 550 mg (1.02 mmol) of the compound obtained in (4) and 34.6 mg (0.102 mmol) of tetrabutylammonium hydrogen sulfate salt in 5 ml of toluene and 5 ml of 25% sodium hydroxide aqueous solution was added 0.41 ml (2.55 mmols) of t-butyl 2bromoacetate. The mixture was stirred at room temperature for 4 hours. The organic layer was removed and the aqueous layer was extracted with 15 ml of hexane. The resulting organic layer was washed with 10 ml of saturated ammonium chloride aqueous solution and then dried over anhydrous magnesium sulfate. The mixture was then filtered and the filtrate was concentrated in vacuo. The resulting concentrate was purified by silica gel column chromatography (developing solvent: hexane: ether=1 : 1) to give 504 mg of 3-oxa-16,17,18,19,20-pentanor-15-cyclohexyl- 13,14-didehydro-PGF2(z t-butyl ester 11,15-bis (tbutyldimethylsilyl ether).

$^1$H-NMR (CDCl$_3$, 300MHz) δ ppm: 0.08 and 0.10 (2s, 12H), 0.88 and 0.89 (2s, 18H), 0.96–1.35 (m, 6H), 1.48 (s, 9H), 1.55–1.93 (m, 8H), 2.09 (ddd, J=5.0 Hz, 6.7 Hz, 14.4 Hz, 1H), 2.26–2.37 (m, 1H), 2.42–2.60 (m, 2H), 3.96 (s, 2H), 4.02–4.13 (m, 3H), 4.18–4.32 (m, 2H), 5.60–5.77 (m, 2H)

$^{13}$C-NMR (CDCl$_3$, 75MHz) δ ppm: 169.5, 133.5, 125.8, 85.8, 83.3, 81.5, 79.7, 72.8, 67.8, 66.5, 52.2, 45.0, 44.1, 43.1, 28.6, 28.0, 26.8, 26.5, 25.9, 25.8, 25.7, 18.2, 17.9, −4.4, −4.8, −5.0, −5.1.

IR (neat): 3480, 2930, 2850, 2230, 1755, 1470, 1375, 1260, 1115, 845, 780 cm$^{-1}$.

(6) To a solution of 518 mg (0.78 mmol) of the compound obtained in (5) in 2 ml of methylene chloride were added 292 mg (2.39 mmols) of N', N'-dimethylaminopyridine and 455 mg (2.39 mmols) of p-toluenesulfonyl chloride. After elevating to room temperature, the mixture was stirred for 5 hours. After adding 20 ml of saturated sodium hydrogencarbonate aqueous solution and 30 ml of hexane thereto, the mixture was stirred for 10 minutes. The organic layer was then removed. The resulting organic layer was dried over anhydrous magnesium sulfate and then filtered. The filtrate was concentrated in vacuo. The resulting crude product was used for the following reaction as it was.

To a solution of the crude product obtained in the above reaction in 8 ml of N,N-dimethylformamide was added 1.11 g (4.83 mmols) of tetra-n-butylammonium chloride. The mixture was stirred at 40° C. for 5 hours. After adding thereto 20 ml of saturated sodium chloride aqueous solution, the mixture was extracted twice with 10 ml each of hexane. The resulting organic layer was dried over anhydrous magnesium sulfate and then filtered. The filtrate was concentrated in vacuo. The resulting crude product was employed for the following reaction without purification.

To a solution of the crude product obtained in the above reaction in 27 ml of acetonitrile were added 1.6 ml of pyridine and 1.35 ml of pyridium poly(hydrogen fluoride) at 0° C. After elevating to room temperature, the mixture was stirred for 4 hours. While stirring, the reaction solution was poured onto a mixture of 30 ml of ethyl acetate and 30 ml of saturated sodium hydrogencarbonate aqueous solution. The organic layer was separated and the aqueous layer was extracted with 20 ml of ethyl acetate. The obtained organic layer was dried over anhydrous magnesium sulfate and then filtered. The filtrate was concentrated in vacuo. The resulting crude product was purified by silica gel column chromatography (developing solvent: ethyl acetate: methanol=50: 1) to give 267 mg of the title compound.

$^1$H-NMR (CDCl$_3$, 300MHz) δ ppm: 0.80–1.35 (m, 6H), 1.47 (s, 9H), 1.60–1.88 (m, 5H), 2.12–2.32 (m, 3H), 2.33–2.48 (m, 3H), 3.96 (s, 2H), 3.90–4.24 (m, 4H), 4.28–4.37 (m, 1H), 5.62–5.78 (m, 2H).

$^{13}$C-NMR (CDCl$_3$, 75MHz) δ ppm: 169.8, 129.9, 128.1, 85.5, 83.1, 81.9, 76.1, 67.8, 67.2, 66.4, 58.8, 54.3, 44.2, 43.4, 28.6, 28.1, 26.4, 25.8.

IR (neat): 3430, 2990, 2930, 2860, 2240, 1740, 1450, 1370, 1245, 1160, 1130, 1045, 845 cm$^{-1}$.

EXAMPLE 2

Preparation of 3-oxa-9-deoxy-9β-chloro-16,17,18,19,20-pentanor-15-cyclohexyl-13,14-didehydro-PGF$_2$ (Compound 2)

To a solution of 261 mg (0.59 mmol) of the compound obtained in Example 1 in 19.6 ml of methanol and 1.96 ml of water was added 124 mg (2.96 mmols) of lithium hydroxide monohydrate. The mixture was stirred at room temperature for 4 hours. After 18 ml of ethyl acetate was added to the mixture, 0.1 N aqueous hydrochloric acid solution was portionwise added thereto to adjust pH to 6.5. Then 5 g of ammonium sulfate was added to the mixture followed by extraction twice with 18 ml each of ethyl acetate. The resulting organic layer was dried over anhydrous magnesium sulfate. The mixture was then filtered and the filtrate was concentrated in vacuo. The resulting crude product was purified by silica gel column chromatography (developing solvent: ethyl acetate: methanol=10 : 1) to give 194 mg of the title compound.

$^1$H-NMR (CDCl$_3$, 300MHz) δ ppm: 0.95–1.40 (m, 6H), 1.41–1.60 (m, 1H), 1.62–1.95 (m, 4H), 2.08–2.31 (m, 3H), 2.32–2.54 (m, 3H), 3.95–4.40 (m, 5H), 4.13 (s, 2H), 5.60–5.85 (m, 2H).

EXAMPLE 3 (Tablet)

In 80 ml of distilled water were dissolved 5 mg of Compound 2 and 500 mg of α-cyclodextrin. The solution was freeze dried. The freeze-dried product, 80 g of crystalline cellulose, 48.5 g of lactose and 10 g of carboxymethyl cellulose were mixed with each other. The mixture was granulated with a fluid bed granulator, using as a binder a solution of 10 g of hydroxypropyl cellulose in 100 ml of purified water. To the granules was added 1 g of magnesium stearate. After blending them, tablets having a weight of 150 mg/tablet were prepared. One tablet contains 5 μg of Compound 2.

EXAMPLE 4 (Capsule)

In 80 ml of distilled water were dissolved 5 mg of Compound 2 and 500 mg of γ-cyclodextrin. The solution was freeze dried. The freeze-dried product, 50 g of crystalline cellulose, 77.5 g of potato starch and 10 g of low substitution hydroxypropyl cellulose were mixed with each other. The mixture was granulated with a fluid bed granulator, using as a binder a solution of 10 g of hydroxypropyl cellulose in 100 ml of purified water. To the granules were added 1 g of hardened oil and 1 g of magnesium stearate. After blending them, 150 mg of the mixture was filled up in No. 3 capsule to obtain a capsule containing 5 μg of Compound 2.

EXAMPLE 5 (Granule)

In 80 ml of distilled water were dissolved 5 mg of Compound 2 and 500 mg of β-cyclodextrin. The solution was freeze dried. The freeze-dried product, 659.5 g of corn starch and 300 g of mannitol were mixed with each other. The mixture was granulated with a fluid bed granulator, using as a binder a solution of 40 g of hydroxypropylmethyl cellulose in 600 ml of purified water to obtain granules containing 5 μg of Compound 2 in 1 g of the granules.

EXAMPLE 6 (Injection)

After 20 g of yolk lecithin was dissolved in 250 g of soybean oil with heating, 1 mg of Compound 2 was added to the solution. Separately, 90 g of glycerine was dissolved in 1.2 liter of sterile water for injection. The solution was mixed with the soybean oil solution described above. After the mixture was emulsified under high pressure, pH was adjusted with sodium hydroxide and sterile water was added to make the volume 2 liters. Then 2 ml of the mixture was packed in an ampoule. The ampoule was sterilized to give an injection containing 1 μg of Compound 2 in one ampoule.

EXAMPLE 7 (Injection)

After 90 g of α-cyclodextrin was dissolved in 1 liter of sterile water for injection. Then 1 mg of Compound 2 and 2 g of citric acid were dissolved in the solution. In an ampoule 1 ml of the solution was packed. The ampoule was freeze dried to give an injection containing 1 μg of Compound 2 in one ampoule.

Industrial Applicability

As will be apparent from the test examples later shown, the compounds of the present invention exhibit a potent platelet aggregation inhibition activity. Furthermore, the compounds of the present invention possess higher selectivity in renal vasodilatory and coronary vasodilatory activities than in systemic peripheral vasodilatory activity, with long duration of the action. The vasodilatory selectivity of the compounds is higher in the renal artery than in the other peripheral artery, even compared with the action of Comparative Drug A (which is a compound corresponding to Compound 2 prepared in Example 2, wherein the 13,14-triple bond is replaced by a double bond and described in Examples of Japanese Patent Application KOHYO No. 2-502009; hereinafter the same), indicating that the compound provides a more potent activity, a longer duration of the action and a more potent platelet aggregation inhibition activity. In Comparative Drug A and the compound of the present invention, peripheral vasodilatory activity in the femoral artery was inhibited by DP receptor antagonist, BWA868C; it is thus reasonably considered that the compound of the present invention would act on prostaglandin $D_2$ receptor. It is also considered that the compound of the present invention would potentiate the renal function because the compound showed an excellent acceleration of glomerular filtration and an excellent diuretic activity.

Accordingly, the compounds of the present invention are useful for the treatment of various renal diseases such as nephritis, nephrosis, renal failure, etc. as well as diseases of the circulatory organs such as ischemic heart disease (angina pectoris), heart failure, hypertension, etc.

For this purpose, the compounds of the present invention are administered orally or parenterally such as intravenously or rectally. For oral administration, the compounds may be used in the form of solid preparations, e.g., tablets, granules, capsules, etc., and liquid preparations, e.g., a solution, a fat emulsion, a liposome suspension, etc. For intravenous administration, the compounds may be used in the form of an aqueous or non-aqueous solution, an emulsion or a suspension, or in the form of solid preparations dissolved in a solvent for injection immediately before use. The compounds may also be used in the form of a suppository for rectal administration, or in the form of a pessary for intravaginal administration. The compounds of the present invention may also be used in the form of pharmaceuticals after forming clathrate or enclosure compounds together with α, β or γ-cyclodextrin or methylated cyclodextrin. The compounds may be used in a daily dose of 0.05 to 60 μg for intravenous or rectal administration, and in a daily dose of 1 to 600 μg for oral administration. If necessary, the daily dose of the compounds may also be given once to 5 times a day.

The effects of the compounds of the present invention are explained below in more detail.

TEST EXAMPLE 1

Inhibition of human platelet aggregation

Blood was collected from human and immediately blended with 1/10 volume of 3.8% sodium citrate aqueous solution. After centrifugation at 180× g for 15 minutes at room temperature, platelet-rich plasma (PRP) was obtained from the supernatant.

Platelet aggregation was determined by a modification of the Born method (Nature, 194, 927, 1962). After one minute incubation of a mixture of 100 μl of PRP and 5 μl of drug solutions in ethanol having various concentrations while stirring at 37° C. at 100 rpm, 5 μl of ADP (4.5 to 12.5 μM) was added to cause platelet aggregation. The maximum aggregation rate was thus determined with an aggregometer.

The aggregation inhibition activity was determined by calculating the aggregation inhibition rate to aggregation obtained when ethanol was used in place of the drug solution and seeking $IC_{50}$ based on the dose-response curves. The activity was evaluated in terms of relative activity to $IC_{50}$ of PGE1 measured at the same time. The results are shown in Table 1.

TABLE 1

| Drug Tested | Aggregation Inhibition Activity |
| --- | --- |
| $PGE_1$ | 1 |
| Control Drug A | 9.7 |
| Compound 2 | 114 |

TEST EXAMPLE 2

Renal vasodilator effect and hypotensive effect

Mongrel dogs of both sexes weighing 7 to 11 kg, four (4) dogs for each group, were anesthetized with sodium pentobarbital (30 mg/kg, i.v.). Femoral arterial blood pressure was measured with a pressure transducer (TP-400T, Nihon Kohden) connected to a tube inserted backwardly into the femoral artery, through an amplifier for strain pressure (AP-630G, Nihon Kohden). The heart rate was measured using a heart rate counter (AT-600G, Nihon Kohden) driven by pressure waves. The left abdominal wall was excised and a probe of an electromagnetic flowmeter (MFV-2100, Nihon Kohden) was inserted into the left renal artery and connected to the electromagnetic flowmeter. The renal blood flow was measured at the peak caused by administration of each drug (Tsuchida et al., Arzneim.-Forsch., 36, 1745, 1986). Each drug was dissolved in ethanol; $PGE_1$, Control Drug A, and the compound of the invention were intravenously given through the femoral vein in doses of 300 to 3000 pmols/kg, 10 to 3000 pmols/kg and 1 to 300 pmols/kg, respectively. The volume given was 1 μl/kg, respectively.

The renal blood flow increasing activity or hypotensive activity of each drug was evaluated by the dose caused 20% increase in the renal blood flow or by the dose caused 10% fall in blood pressure, in terms of potency ratio when the activity of Control Drug A was made 1.

The results are shown in Table 2.

TABLE 2

| | Potency Ratio | |
| --- | --- | --- |
| Drug Tested | Renal Blood Flow Increasing Activity | Hypotensive Activity |
| $PGE_1$ | 0 | 2 |
| Control Drug A | 1 | 1 |
| Compound 2 | 50 | 20 |

TEST EXAMPLE 3

Acceleration of glomerular filtration and diuretic activity

Method

Beagle dogs of both sexes, weighing 7 to 10 kg, were anesthetized with sodium pentobarbital (30 mg/kg), six (6) dogs for each group, the animal was fixed for artificial respiration, lying down on one side. The right ascending artery was cannulated with a tube for measurement of blood pressure, the right radial skin vein with a tube for drug administration and for constant infusion of creatinine and the left saphenous vein with a tube for collecting blood, respectively. The left abdominal wall was excised and cannulated with a tube for collecting urine was inserted into ureter (blood pressure and heart rate were determined as in Test Example 2).

The following experiment was performed according to the method of Levinsky and Levy (Handbook of Physiology, Section 8: Renal Physiology, page 103, 1973, American Physiological Society).

At the onset of the experiment, creatinine was intravenously administered constantly in a dose of 100 mg/kg; immediately thereafter 1 ml/min of creatinine-physiological saline was infused to keep the creatinine level at 50 mg/kg/hr. After the blood pressure, heart rate, renal blood flow and volume of urine were almost stabilized, urine was collected every 10 minutes, taking 10 minutes as one fraction. Blood was collected in the middle of each fraction to obtain plasma.

The drug was infused at 10 minutes interval through the femoral vein at 5 µl/kg/min, while continuously increasing the dose.

The glomerular filtration rate was calculated according to the following equation.

Glomerular filtration rate: $GFR$ (ml/min) = concentration of creatinine in urine × volume of urine/concentration of creatinine in plasma

Each drug was prepared in the following dose in a volume of 5 µl/kg/min by diluting 0.022M ethanol solution with physiological saline. Each drug was infused for 10 minutes. $PGE_1$: 10–300 pmols/kg/min, Control Drug A: 10–300 pmols/kg/min, Compound of the invention: 1–30 pmols/kg/min.

Results $PGE_1$ showed, in any dose, no increase in renal blood flow, volume of urine and glomerular filtration rate. On the other hand, all of the parameters above dose-dependently increased in Control Drug A and the compound of the invention. When the increase in renal blood flow, volume of urine and glomerular filtration rate was calculated in terms of dose ratio for increasing 30%, 20% and 20%, respectively, the compound of the present invention showed the potency by 10, 10 and 30 times higher than those of Control Drug A.

TEST EXAMPLE 4

Coronary vasodilator effect

Method

Beagle dogs of both sexes, weighing 7 to 10 kg, six (6) dogs for each group were anesthetized with sodium pentobarbital (30 mg/kg, i.v.). Femoral arterial blood pressure was recorded on a recorder (WI- 681G, WT-685G, Nihon Kohden) with a pressure transducer (MPU-0.5, Nihon Kohden) connected to a tube inserted backwardly into the femoral artery, through a strain pressure amplifier (AP-620G, AP-621G, Nihon Kohden). Coronary blood flow was determined based on the method of Winbury et al. (J. Pharmacol. Exp. Ther., 168, 70, 1969). After a thoracotomy under artificial respiration, the anterior descending branch of the left coronary artery was isolated for placement of a flow probe around the vessel. The probe for blood flow measurement (FR-1.5, 2, Nihon Kohden) was fixed the artery. The probe was connected to an electromagnetic flowmeter (MFV-2100, Nihon Kohden) for measurement. A femoral vein was cannulated for injection of the drug. Each drug was dissolved in ethanol; $PGE_1$, Control Drug A, and the compound of the invention were intravenously administered in doses of 0.3–10 nmols/kg, 0.3–10 nmols/kg and 0.1–1 nmol/kg, respectively. A volume of each drug given was 1 µl/kg. The coronary vasodilator rate is expressed in terms of reduction in resistance of the coronary vessel (coronary blood flow/mean blood pressure). The drug potency rate was determined from a dose of each drug for 20% fall in the resistance of the coronary vessel.

Results

The compound of the present invention showed the reduction in the resistance of the coronary vessel by twice higher than $PGE_1$ and 10 times higher than Control Drug A.

We claim:

1. A prostaglandin derivative represented by formula:

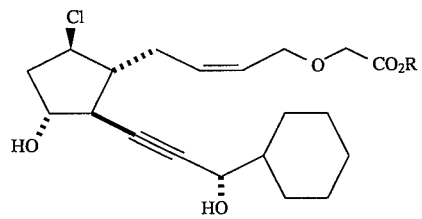

wherein R represents a hydrogen atom or an alkyl group having 1 to 6 carbon atoms, and a salt thereof.

2. A composition for improving renal diseases comprising as an effective ingredient a prostaglandin derivative represented by formula:

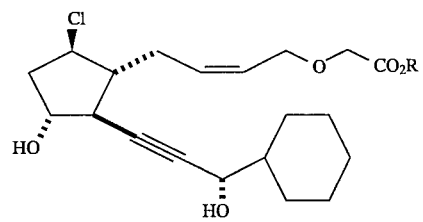

wherein R represents a hydrogen atom or an alkyl group having 1 to 6 carbon atoms, and a salt thereof.

3. A composition for improving ischemic heart diseases or heart failure comprising as an effective ingredient a prostaglandin derivative represented by formula:

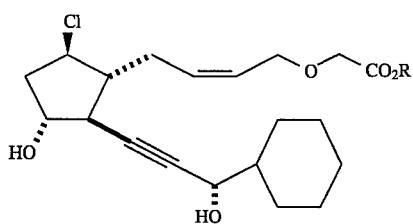
wherein R represents a hydrogen atom or an alkyl group having 1 to 6 carbon atoms, and a salt thereof.
* * * * *

UNITED STATES PATENT AND TRADEMARK OFFICE
CERTIFICATE OF CORRECTION

PATENT NO. : 5,491,254

DATED : February 13, 1996

INVENTOR(S) : SATO et al

It is certified that error appears in the above-indentified patent and that said Letters Patent is hereby corrected as shown below:

Col. 1, line 24, "supra" should read --_supra_--.

Col. 2, line 2, "supra" should read --_supra_--.

Col. 3, line 45, "w-side" should read --ω-side--; and
line 50, "s-side" should read --α-side--.

UNITED STATES PATENT AND TRADEMARK OFFICE
CERTIFICATE OF CORRECTION

PATENT NO. : 5,491,254
DATED : February 13, 1996
INVENTOR(S) : Sato et al

It is certified that error appears in the above-indentified patent and that said Letters Patent is hereby corrected as shown below:

Col. 6, line 16, after "m,", last instance, insert --2H)--;
      line 37, "dr" should read --dt--;
      line 58, ""PGF2(z" should read --PGF2-α--; and
      line 59, "(tbutyldimethylsilyl" should read
--(t-butyldimethylsilyl--.

Col. 10, line 2, "194" should read --194--; and
      line 44, "36" should read --36--.

Col. 12, line 9, "168" should read --168--.

Signed and Sealed this

Fifteenth Day of October, 1996

Attest:

BRUCE LEHMAN

Attesting Officer     Commissioner of Patents and Trademarks